(12) United States Patent
Will et al.

(10) Patent No.: US 11,617,667 B2
(45) Date of Patent: Apr. 4, 2023

(54) PROSTHESIS SOCKET AND METHOD FOR CONTROLLING AN ADJUSTMENT OF AN INNER CIRCUMFERENCE OF A PROSTHESIS SOCKET

(71) Applicant: OTTOBOCK SE & CO. KGAA, Duderstadt (DE)

(72) Inventors: Christian Will, Gottingen (DE); Lars Benjamin Finke, Landolfshausen (DE); Sebastian Betz, Gottingen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 85 days.

(21) Appl. No.: 16/099,618

(22) PCT Filed: May 8, 2017

(86) PCT No.: PCT/EP2017/060941
§ 371 (c)(1),
(2) Date: Nov. 7, 2018

(87) PCT Pub. No.: WO2017/194479
PCT Pub. Date: Nov. 16, 2017

(65) Prior Publication Data
US 2019/0183663 A1 Jun. 20, 2019

(30) Foreign Application Priority Data
May 10, 2016 (DE) .......................... 102016108631.2

(51) Int. Cl.
*A61F 2/80* (2006.01)
*A61F 2/76* (2006.01)
(Continued)

(52) U.S. Cl.
CPC .................. *A61F 2/76* (2013.01); *A61F 2/54* (2013.01); *A61F 2/60* (2013.01); *A61F 2/80* (2013.01);
(Continued)

(58) Field of Classification Search
CPC ........................................................ A61F 2/80
See application file for complete search history.

(56) References Cited

U.S. PATENT DOCUMENTS 8,978,224 B2 * 3/2015 Hurley ...................... A61F 2/54
29/407.1
2010/0042227 A1 2/2010 Schmidt
(Continued)

FOREIGN PATENT DOCUMENTS

| CN | 101938958 A | 1/2011 |
|---|---|---|
| CN | 104053416 A | 9/2014 |

(Continued)

OTHER PUBLICATIONS

PCT International Search Report for PCT International Patent Application No. PCT/EP2017/060941, dated Oct. 2, 2017.

*Primary Examiner* — David H Willse
(74) *Attorney, Agent, or Firm* — Holland & Hart LLP

(57) ABSTRACT

A prosthesis socket having a proximal insertion opening and an inner circumference which at least partially surrounds a limb stump, at least one connection device for a prosthesis component, which is connectable to the prosthesis socket, at least one actuator operable to change the inner circumference of the prosthesis socket, and at least one sensor coupled to a control device, wherein the control device is connected
(Continued)

to the actuator and activates or deactivates same, depending on the received sensor signals, and to a method for adjusting the inner circumference.

20 Claims, 8 Drawing Sheets

(51) Int. Cl.
*A61F 2/54* (2006.01)
*A61F 2/60* (2006.01)
*A61F 2/74* (2006.01)
*A61F 2/50* (2006.01)
*A61F 2/78* (2006.01)
*A61F 2/68* (2006.01)
*A61F 2/70* (2006.01)

(52) U.S. Cl.
CPC ........... *A61F 2/74* (2021.08); *A61F 2002/503* (2013.01); *A61F 2002/5026* (2013.01); *A61F 2002/5027* (2013.01); *A61F 2002/5036* (2013.01); *A61F 2002/6836* (2013.01); *A61F 2002/6863* (2013.01); *A61F 2002/701* (2013.01); *A61F 2002/763* (2013.01); *A61F 2002/764* (2013.01); *A61F 2002/7625* (2013.01); *A61F 2002/7635* (2013.01); *A61F 2002/7862* (2013.01)

(56) References Cited

U.S. PATENT DOCUMENTS

| | | |
|---|---|---|
| 2010/0274364 A1 | 10/2010 | Pacanowsky et al. |
| 2011/0071647 A1 | 3/2011 | Mahon |
| 2011/0087339 A1 | 4/2011 | Pusch et al. |
| 2012/0209404 A1 | 8/2012 | Astilla et al. |
| 2012/0271433 A1 | 10/2012 | Galea et al. |
| 2013/0123940 A1 | 5/2013 | Hurley et al. |
| 2013/0218296 A1 | 8/2013 | Koniuk et al. |
| 2013/0245785 A1 | 9/2013 | Accini et al. |
| 2014/0068838 A1 | 3/2014 | Beers et al. |
| 2014/0121783 A1 | 5/2014 | Alley |
| 2016/0000583 A1 | 1/2016 | Ballas et al. |
| 2016/0000587 A1 | 1/2016 | Hurley et al. |

FOREIGN PATENT DOCUMENTS

| | | | |
|---|---|---|---|
| CN | 104884005 A | 9/2015 | |
| DE | 102006046928 A1 | 4/2008 | |
| DE | 102010019843 A1 | 11/2011 | |
| JP | 2015-502200 A | 1/2015 | |
| WO | 2013191933 A2 | 6/2013 | |
| WO | 2014018736 A1 | 1/2014 | |
| WO | 2014144985 A1 | 9/2014 | |
| WO | WO 2016/091763 A1 * | 6/2016 | ............... A61F 2/80 |

* cited by examiner

PROSTHESIS SOCKET AND METHOD FOR CONTROLLING AN ADJUSTMENT OF AN INNER CIRCUMFERENCE OF A PROSTHESIS SOCKET

TECHNICAL FIELD

The invention relates to a prosthesis socket with a proximal insertion opening and an inner circumference which at least partially surrounds a limb stump, at least one connection device for a prosthesis component, which is connectable to the prosthesis socket, and at least one actuator, by means of which the inner circumference of the prosthesis socket is changeable. The invention also relates to a method for controlling an adjustment of an inner circumference of such a prosthesis socket.

BACKGROUND

Prosthesis sockets are used for receiving limb stumps, for example, amputation stumps, and they ensure that additional prosthesis components are held securely on the remaining extremity. In order to ensure a secure fastening of the prosthesis socket on the limb stump, various connection concepts have been developed. One concept essentially provides a closed dimensionally-stable envelope provided with an insertion opening into which the limb stump provided with a prosthesis liner is introduced. The prosthesis socket is then held by negative pressure on the liner.

An additional possibility consists in equipping a prosthesis liner with a mechanical locking device, for example, a pin, which is introduced into a recess within the prosthesis socket and locked there by positive connection. The two connection concepts have in common that the inner contour of the prosthesis socket should correspond as precisely as possible to the outer contour of the limb stump with an allowance for the liner. In order to achieve this, a limb stump imprint is taken, a positive model of the limb stump is prepared, and, using this model, an individual prosthesis socket is produced from a plastic which is usually fiber-reinforced.

In addition to such sockets which are closed in circumferential direction, prosthesis sockets are known which are designed to be adjustable in radial direction. DE 10 2010 019 843 A1 relates to a prosthesis socket with a distal end piece and connection devices for a prosthetic knee joint and a radially tensionable envelope as well as a tensioning device for adjusting a recess space of the envelope on the limb stump. The envelope can comprise at least two segments which are connected to a support frame and which overlap over one another in sections. The tensioning device has at least one cable pull which extends over the segments and is adjustable by means of a setting device in terms of the effective length.

DE 10 2006 046 928 A1 relates to a prosthesis socket with a flexible inner socket and a stable outer socket which comprises a distal end piece, from which shell segments extend proximally forming a gap between themselves. The shell segments can be connected to the distal end piece in such a manner that they can be pivoted against a resilient resistance from a starting position. Between the shell segments, a traction element delimiting the relative pivoting movement can be provided for bridging the gap between the shell segments. An adjustment of the contact pressure by means of the traction element does not occur; the traction element only prevents excessive pivoting of the shell segments apart from one another.

WO 2013/191933 A2 relates to an orthetic device with a treatment regimen. The orthetic device, in particular a lumbar orthetic device, comprises a tensioning device for a tensioning means as well as a motor drive. The tensioning device moves two orthetic segments towards one another or relaxes the tensioning device, so that the orthetic segments can be moved apart from one another by an applied reset force. The orthetic segments are coupled to one another in the abdominal area by means of a hook-and-loop fastener; in the back area, the tensioning device which automatically tensions or relaxes the orthetic device is arranged. Pressure sensors are arranged in the orthetic device in order to measure the tension. In addition, if changes in the position of the user are detected, the tension of the tensioning device is automatically adjusted. By periodic tensioning and relaxation of the tensioning device, a massage function can be provided.

US 2014/0068838 A1 relates to a motor-driven tensioning device for shoes, posture correcting devices, backpacks, headgear or orthetic devices. The motor sets the desired tension by means of a tensioning means, for example, a cable or a rope. The tension can be set by means of a remote control.

The securing of the prosthesis socket to a limb stump, possibly to a liner, can be difficult, in particular for patients receiving multiple treatments, who are limited in terms of their manual skills.

SUMMARY

The aim of the present invention is to provide a prosthesis socket and a method which allow a simple putting-on.

According to the present disclosure, this aim is achieved by a prosthesis socket and by a method having the features disclosed herein. Advantageous embodiments and developments of the present disclosure are disclosed in the description and the figures.

The prosthesis socket with a proximal insertion opening and an inner circumference which at least partially surrounds a limb stump, at least one connection device for a prosthesis component, which is connectable to the prosthesis socket, and at least one actuator, by means of which the inner circumference of the prosthesis socket is changeable, provides at least one sensor which is coupled to a control device, wherein the control device is connected to the actuator and activates or deactivates same depending on the received sensor signals.

The coupling of an actuator for changing the inner circumference of a prosthesis socket to a sensor by means of a control device, in such a manner that the actuator is activated or deactivated depending on received sensor signals, enables an automatic tensioning or relaxation of the prosthesis socket or of the contact force of the prosthesis socket on the limb stump, so that, for example, the prosthesis socket can be opened or closed, in order to facilitate the taking-off and the putting-on, and to enable an automatic putting-on. In addition, it is possible to compensate automatically or deliberately for variations in the volume within the limb stump, in that the inner circumference is increased in order to reduce the contact pressure, for example, when the limb stump volume increases during the wearing time. In the same way, when special loads are detected, for example, during sports activities, it is possible to reduce the inner circumference in order to provide a firmer contact of the prosthesis socket on the limb stump. In addition, periodic changes of the inner circumference can be carried out, in order to achieve a massage effect. Moreover, when rest phases are detected, for example, during sitting, the inner circumference can be increased automatically. The opening and closing of the prosthesis socket can thus occur automatically.

The actuator can be designed as a drive for a pump, a sliding element, a lever, a winding device for traction means, a spreading element, a gear, as a drive for activating a shape memory alloy or an electroactive polymer, or as a switchable magnet. In particular, the actuator can be designed as a motor and, for example, drive a tensioning device which comprises, for example, a traction means such as a belt, a rope, a band, a cable or a braid and which increases or decreases the effective length thereof and thereby changes the inner circumference of the prosthesis socket. In principle, it is also provided that the actuator can be operated manually or controlled manually, for example, by a switch, so that no control device and no sensor needs to be present. The at least one actuator can also drive a pump, by means of which a changeable volume which is arranged or formed in the prosthesis socket is changed. Thus, for example, when a prosthesis socket is closed, a volume arranged on the inner side can be present, which can be filled with pressurized air or a hydraulic fluid provided in an external reservoir, in order to change the inner circumference in this way. For this purpose, the prosthesis socket has to have a counter-bearing which, for example, is provided by the closed cross section or else by a rigid tensioning device or delimitation device, for example, a fixedly set traction means. It is equally possible that, by means of a change in volume, in the case of a multi-part prosthesis socket with several support elements which can be moved relative to one another, a change in inner circumference is carried out. This can occur either by applying a shifting force to the support elements by means of the changing volume, for example, by inflation, or by filling a volume pressing against a counter-bearing, or else by an increase in internal volume. It is also possible to mechanically increase the volume, for example, by setting up hinged levers or fibers which assume a setup position in the case of a shifting of, for example, a slider, and which press against a volume wall and thereby bring about a volume change of the volume. It is equally possible that a ring placed around the prosthesis socket is mounted in a longitudinally slidable manner. Due to a conical design of the prosthesis socket or a conical design of a ring guide on the external side, by means of a longitudinal sliding, support elements which are part of a multi-part prosthesis socket can be moved towards one another or apart from one another. Thereby, an inward pivoting or an outward spreading movement can be implemented. In addition to a multi-part design of the prosthesis socket, it is also possible to design the prosthesis socket as a single part and to provide it with a slit, optionally with overlapping side edges, in order to enable a complete enclosing of the prosthesis limb stump and at the same time enable a change in circumference. The prosthesis socket is then designed in the shape of a coil, which results in a change of the inner circumference, in that the winding angle or overlap angle of the two side edges is changed.

It is equally possible that the actuator is designed as a switchable magnet, by means of which a corresponding adjusting of mechanical, magnetorheological and other components can occur.

In a variant of the invention, it is provided that the prosthesis socket with a proximal insertion opening and an inner circumference which at least partially surrounds a limb stump, with at least one connection device for a prosthesis component, which is connected to the prosthesis socket, comprises at least one actuator, by means of which the inner circumference of the prosthesis socket is enlargeable. The actuator can be driven or is driven manually or by a motor, so that it is possible to carry out a widening of the inner circumference of the prosthesis socket, that is to say the opening of the prosthesis socket, even without a sensor. The above explanations regarding a circumference increase in connection with a sensor apply accordingly to such a prosthesis socket, but without a sensor or control device having to be provided. A motor drive can be activated or deactivated by a prosthesis user by means of a switch, a remote control or the like, in order to increase the inner circumference of the prosthesis socket. Manual actuation or the ability to actuate the actuator decreases the weight of the prosthesis socket and enables a simple increasing of the inner circumference by manual adjustment or manipulation of the actuator.

In particular, it is provided that such a prosthesis socket is used with an actuator which increases the inner circumference when a prosthesis socket is held by a resilient reset force on the limb stump. The resilient reset force is formed by the prosthesis socket wall itself or by the support elements. In the same way, a resilient mounting of the support element or of the prosthesis socket wall can apply the resilient reset force in the direction of the limb stump, that is to say in the direction of a decreasing inner circumference. The desired inner diameter is set and achieved by the margin of the opening of the prosthesis socket by the actuator. The opening can occur manually or by motor with manual control. In the same way, it is possible that the opening is carried out automatically after the detection of corresponding sensor values such as position, position in the socket, position of the socket, pressure, duration of a pressure, pressure changes, oxygen saturation, blood flow, temperature or the like. After the opening, in particular after a complete opening, the prosthesis socket can be pulled over the limb stump or the limb stump can be inserted in the prosthesis socket. By a reduction of the force applied for the opening, for example, of a correspondingly deflected traction force, by means of a spreading element which is moved along a slot or by means of a ring which is moved along a conically shaped socket, the contact force applied to the limb stump is set, and the socket is adjusted to the limb stump. An active actuation thus occurs only in the direction of the opening of the socket; the reset in the direction of the limb stump, and consequently a reduction of the inner circumference, occur passively due to a resilient design or mounting of the support elements or of the prosthesis socket wall.

In particular, the prosthesis socket is designed in multiple parts, with at least two support elements which receive the limb stump between themselves, wherein the support elements enclose the limb stump completely or at least partially so that said limb stump is received firmly in the prosthesis socket. The support elements can be designed to overlap over one another.

At least one tensioning device can be arranged on the prosthesis socket in order to change its inner circumference. The tensioning device can be designed as a traction means, a pneumatically or hydraulically driven spreading or tensioning means, as a longitudinally slidable spreading or closing element, as a movable ring, as a tilting element or as an acceptable actuation element. The respective tensioning means is activated or deactivated by the actuator, optionally with insertion of gears, a force transmission device or the like.

The actuator, for example, in the form of a manual drive or a motor drive of a tensioning device, facilitates the putting-on of the prosthesis socket tremendously. There is no need to manually apply laces, actuate tensioning devices or lock mechanical connection devices or the like. Instead, in the case of a motor-driven actuator, the inner circumference is set to the desired tension, for example, by means of the tensioning device or the changeable volume of the tensioning device, without having to use manual force.

The at least one tensioning device can be designed as a belt, a rope, a band, a cable or a braid or comprise such a tensioning element. In principle, all traction force-transmitting tensioning elements are appropriately usable, including compressively rigid tensioning devices or tensioning devices such as rods, clips or rings. Flexible tensioning devices have the advantage that they can be adjusted more easily to changing circumferences and are overall easier to handle. In addition to flexible tensioning devices, which are advantageously not resilient, toothed belts, perforated belts or chains can also be used as tensioning devices or tensioning elements.

The tensioning element transmitting at least one traction force can be guided in eyelets, channels and/or around at least one deflection roller, in order to achieve, for example, a force/stroke conversion similar to a pulley. Due to the deflection of flexible tensioning elements, the point of application of the tensioning force can be defined. By means of a plurality of deflection rollers, the tensioning force can be distributed multiply, and thus an even pressure distribution can be achieved. In addition, by means of deflection rollers, it is possible to apply tensioning forces at several sites using only one tensioning device, whereby the number of parts is decreased and a simplified assembly can be achieved. Due to the guiding within channels which can be within the socket, for example, in the support elements, the risk that clothing items or other objects become stuck between the tensioning device and the support element is decreased. In the same way, it is possible to bring about a spreading of the prosthesis socket by a deflection of the tensioning element, so that, by rolling up or winding, an increase in the inner circumference can be brought about. For this purpose, the tensioning element is guided around a deflection site which lies beyond the connection site to which the free, non-wound end is connected. Thereby, during winding, one support element is pulled away from another support element, for example.

Several actuators or tensioning devices can be arranged independently of one another along the proximal-distal extent of the prosthesis socket, in order to be able to set independently of one another different contact pressures on the limb stump by a change in the inner circumference of the socket.

The at least one tensioning device is advantageously arranged so that it acts in circumferential direction of the limb stump, in order to bring about in this way a radially acting contact pressure of the support element or of the support elements on the limb stump. In the case of a single-part design of the prosthesis socket with the socket wall as support element, the tensioning device has a winding effect or the overlap is increased, so that the inner circumference is decreased; alternatively, in a counter-current movement, the inner circumference is at least partially increased, so that the socket is loosened or opened.

The support elements or the socket wall itself can be designed to be resilient, for example, in order to provide a reset force during a relaxation of the tensioning device, which makes it possible for the prosthesis socket to open automatically, and thus the patient can easily take off the prosthesis socket. In the same way, conversely, a pretensioning acting on the limb stump can be applied by the socket wall or the support elements, wherein said pretensioning is eliminated by a spreading device, making it possible to take off the socket or to reduce the force acting on the limb stump. The support elements can also be mounted resiliently on the end piece, for example, by an articulation against a spring force. In the same way, it is possible that the support elements are designed so as to form a single part with the end piece, and, for the closing of the prosthesis socket or for putting on the prosthesis socket, they are moved towards one another from a starting position located at a distance.

In order to achieve the most even possible contact pressure of the socket wall or of the support elements acting on the limb stump, said socket wall or support elements can be designed so that they overlap over one another in circumferential direction, so that, at least in the put-on, tensioned state, the prosthesis socket is applied completely around the limb stump and forms a nearly closed cross section. Thereby, parts of the limb stump are prevented from being pushed through a free space between the support elements or in the socket wall, when the inner circumference is decreased.

The socket wall or the support elements can be loaded in a direction away from one another with a spring force or, in the untensioned state, they can be arranged so that they widen conically in proximal direction whereby the entering in the socket or the putting of the prosthesis socket on the limb stump is facilitated. In the untensioned state, this thus results in a funnel shape or a conically widened shape which facilitates the insertion of a limb stump. It is only after the insertion of the limb stump in the prosthesis socket that the tensioning device is tensioned by means of the actuator or the spreading device is moved back, whereby the inner circumference is decreased and, for example, the support elements are moved in a direction towards one another against a spring force or against a resilient reset force due to the material deformation, so that the prosthesis socket is in firm contact with the limb stump.

In the prosthesis socket, a distal contact switch or sensor for the detection of an inserted limb stump can be arranged. The distal contact switch or distal sensor detects whether the limb stump is inserted completely or at least up to a predetermined point in the prosthesis socket. To the extent that the contact switch or sensor detects the corresponding position of the limb stump, the actuator can be activated or deactivated automatically in order to reduce the inner circumference, whereby a self-closing or self-contacting prosthesis socket can be produced. The prosthesis socket then adjusts automatically to the outer contour of the limb stump. The distal contact switch or sensor is advantageously arranged on the end piece which also forms the distal closure of the insertion space of the limb stump, but which can also be arranged above it.

A development of the invention provides that at least one motor current sensor or an internal pressure sensor for the acquisition of the pressure applied by a support element on the limb stump is arranged on the socket wall or on the support element. Internal pressure sensors determine the contact pressure of the support element on the limb stump. For this purpose, it is appropriate to arrange the pressure sensor on the inner side, that is to say on the side of the socket wall or of the support element facing the limb stump. Alternatively to a direct pressure measurement, it is possible and provided to measure the motor current by means of a motor current sensor, the motor current being proportional to the motor torque and thus also proportional to the force with which the tensioning device is tensioned or the inner circumference is reduced. Thereby, it is possible to conclude that there is contact pressure of the support element on the limb stump or that there is socket inner pressure. By means of the sensor(s), it is possible to achieve an optimized pressure distribution and thus an optimized seating of the prosthesis socket on the limb stump. In particular, in combination with a distal contact switch which activates the motor drives, it is possible to perform an automatic closing or opening after the simple insertion of the limb stump in the prosthesis socket. The pressure sensors or motor current sensors acquire the pressure on the limb stump. If the pressure exceeds or reaches a set value, the further tensioning of the tensioning device or the reduction of a spreading is stopped by means of a control device. Thus, the contact pressure provided is always reached when entering or putting on the prosthesis socket. If the socket inner pressure changes, for example, due to variations in volume resulting from longer lasting loading or positional changes, this is detected by means of the pressure sensors or the motor current sensor. The possibility then exists to accordingly loosen or tighten either the tensioning device or the spreading device, or the other devices changing the inner circumference, in order to compensate for an increase in volume or a reduction in volume in the limb stump.

Multiple pressure sensors can be arranged in a proximal-distal distribution on the socket wall or on at least one support element. In the case of multiple motors, multiple motor current sensors can be arranged on the prosthesis socket, so that an adjusted pressure can be set independently of one another by means of the proximal-distal extent of the prosthesis socket. Pressure and motor current sensors can also be used in combination. Moreover, oxygen saturation sensors, blood flow sensors and/or temperature sensors can be used.

In principle, it is possible to tension the tensioning device or also multiple tensioning devices by means of a motor. A tensioning of the tensioning device, which can be set independently of one another, occurs advantageously by means of multiple motors arranged on the prosthesis socket. Using a motor, tensioning devices acting independently of one another can in fact be set, but the exerted tensioning force of the tensioning devices is not independent of one another, and, while different adjustment paths of the tensioning devices can be implemented by means of gears, these adjustment paths are, however, coupled to one another in the case of only one motor. Using multiple motors, an individual setting of the multiple tensioning devices is possible, whereby different pressure distribution characteristic lines, pressure patterns or also alternating compressive forces can be implemented during the wearing.

On the prosthesis socket, at least one control device for the activation or deactivation of the at least one actuator, in particular a motor, can be arranged. The control device can be actuatable directly with a switch, by gesture control or by remote control, in order to perform the opening function or closing function, for example, at the touch of a button. The control device can also be activated by means of other signals, for example, acoustic signals, movement patterns or another type of remote control.

At least one position angle sensor, angle sensor, acceleration sensor, switch, oxygen saturation sensor, blood flow sensor, temperature and/or inertial sensor, which is/are coupled to the control device, can be arranged on the prosthesis socket or on a connected prosthesis component. By means of the sensors, the current conditions of use of the prosthesis can be acquired, and an adjustment of the pressure depending on the conditions of use can be carried out. For example, if a particularly high level of activity is detected, the contact pressure can be increased and the tensioning device can be tensioned, in order to ensure an optimal hold. During pauses in activity, the contact pressure can be reduced. In the same way, for at-risk users, it is possible to automatically reduce the contact pressure after a certain time, for example, for diabetics, in order to prevent that excessively high pressures are applied to the limb stump for an excessively long time period. Thereby, a predetermined wearing time limit can be implemented. The reduction of the pressure can be displayed or output, for example, optically, acoustically or haptically. In the socket or in a separate component such as a tablet, a mobile telephone, a display element or a warning device, there is a feedback system for the patient. The feedback system, in the form of an app, a lamp, a vibration generator or the like, can provide the patient with feedback. Feedback on an excessively high pressure on the limb stump or on an excessively long time period is particularly important for diabetics who in some cases have reduced pain sensation or a high risk of vasoconstriction. During sitting as well, the contact pressure can be reduced automatically; when the prosthesis is used again, for example, in the case of prostheses of the lower extremities, during getting up or during walking, the pressures are automatically increased. For the acquisition of the position of the limb stump in the socket, pressure sensors or contact sensors can be used, the latter similarly to a touch screen.

A ratchet or a tensioning lever can be associated with the actuator or the tensioning device in order to mechanically bring about a locking in the set position.

Moreover, it is possible to arrange a mechanical unlocking device on the prosthesis socket, in order to make it possible to take off the prosthesis socket, for example, in the case of a failure of the energy supply for the actuators or motors. In the closed state, the contact pressure applied upon pressure application can decrease in proximal direction, in order to avoid undesired blood stasis in the distal area of the limb stump.

In a development of the invention, it is provided that the prosthesis socket is produced in a 3D printing process. An end piece, if present, the support elements and/or the socket wall are produced in the 3D printing process.

In the same way, additional components of the prosthesis socket can be produced in a 3D printing process, for example, the tensioning elements such as pull strings, belts or levers, the eyelets or tunnels for guiding tensioning elements, guides, spreading elements, actuators or recesses for actuators. Thereby, a plurality of components can be integrated in the prosthesis socket.

The method for controlling an adjustment of the inner circumference of a prosthesis socket, as described above, provides that, in the case of detection of a predetermined position of the limb stump, for example, a predetermined spatial position or a predetermined position within the prosthesis socket and/or in the case of detection of a compressive force exerted on the limb stump or the at least one sensor, the actuator is activated or deactivated automatically. The tensioning device is tensioned or relaxed, for example, automatically by a motor. Thereby, the putting on and taking off of the prosthesis socket is automated and simplified.

A development of the invention provides that the tensioning device is tensioned only up to a predetermined contact pressure; the contact pressure is monitored by a sensor, for example, by direct pressure sensors or motor current sensors.

The contact pressure of the support elements on the limb stump can be acquired, wherein the contact pressure is changed depending on the activity, an amount of time, a position of the prosthesis socket or a change in contact pressure. If high acceleration forces on the prosthesis socket occur, for example, due to increased activity during sport, the contact pressure can be increased. If a certain contact pressure is applied beyond a certain time span, a contact pressure reduction can be initiated by means of a time signal, in order to prevent damaging the tissue of the limb stump. If the prosthesis socket is in a certain position, for example, in a horizontal position in the case of prosthesis sockets of lower extremities, and if this position is maintained for a certain time period, it can be concluded that there is a certain activity, for example, sitting or lying, so that a reduction of the contact pressure can be carried out. If the contact pressure changes above a threshold value, for example, due to an increase in volume or a reduction in volume, an adjustment of the contact pressure can also be initiated, in order to approximate a contact pressure which has been fixed once and optimized to the extent possible.

For the opening of the prosthesis socket, support elements can be moved away from one another by the actuator, so that the prosthesis socket is actively opened by the actuator in order to increase the inner circumference. The same can occur in the case of a design with a prosthesis socket wall, in that the socket wall is pulled apart, moved apart, pressed apart or spread apart by the actuator, so that a slot is enlarged or an overlap is reduced. Alternatively or additionally, for the change in circumference, a tensioning device acting against a resilient pretensioning force of the support elements or of the socket wall can be relaxed. In the process, the prosthesis socket is widened by the resilient behavior of the support elements, of the socket wall or its mounting, which can be exposed to a pretensioning force in the direction of an increased inner circumference.

Additionally or alternatively, for closing the prosthesis socket or for reducing the inner circumference, support elements or a socket wall of the prosthesis socket are moved on one another by the actuator or by its resilient behavior from a widened position into a tensioned position with an inner circumference which is reduced in comparison to the starting position. The closing occurs actively by means of an actuator which activates a closing device or moves the support elements towards one another or moves a socket wall together. This can occur by means of tensioning elements or by means of the sliding of at least one slider, clip or ring. Alternatively or additionally, the support elements, the socket wall or its mounting can be designed to be resilient, so that in the case of elimination of a spreading force or a lock, the inner circumference is reduced by the resilient behavior.

In a variant of the invention, it is provided that, for the adjustment of the inner circumference of a prosthesis socket, the prosthesis socket is opened, for example, in that support elements are moved apart from one another by an actuator, a socket wall is pulled apart or, for the change in circumference, a tensioning device acting against a resilient pretensioning force of the support elements or of the socket wall is relaxed. The opening of a prosthesis socket with a changeable inner circumference occurs either manually or by motor by active movement apart from one another of components of a prosthesis socket, for example, movable support elements, or by pulling apart of a socket wall, for example, by widening a slot or by a reduction of an overlap angle of an overlapping socket wall. It is also possible that, for the change in circumference, a tensioning device is relaxed, wherein the tensioning device acts against a resilient pretensioning force of the support elements of the socket wall. The opening of the prosthesis socket can thus also occur without a sensor.

Preferably, the actuator actively acts by means of spreading elements, traction elements, a tensioning device or the like against a pretensioning force which acts in the direction of a reduction in the circumference of the prosthesis socket. Due to the resilient reset force of the support elements or of the socket wall, the socket is held on the limb stump. The required contact force or holding force is applied by the reset force. The setting of the contact pressure or of the optimal inner circumference is brought about by an adjusted opening or yielding of the actuator against the inwardly acting pretensioning force. If the prosthesis socket is sufficiently open, in particular completely open, the limb stump can be inserted in the inner circumference, and, by decreasing a traction force, as a result of moving a spreading element or releasing a lock, the socket is adjusted to and pressed against the limb stump by the reset force. The prosthesis socket is opened actively, and the reset occurs passively by the pretensioning force.

BRIEF DESCRIPTION OF THE DRAWINGS

Below, embodiment examples of the invention are explained in greater detail in reference to the appended figures. In the drawings.

DETAILED DESCRIPTION

Figure 1:
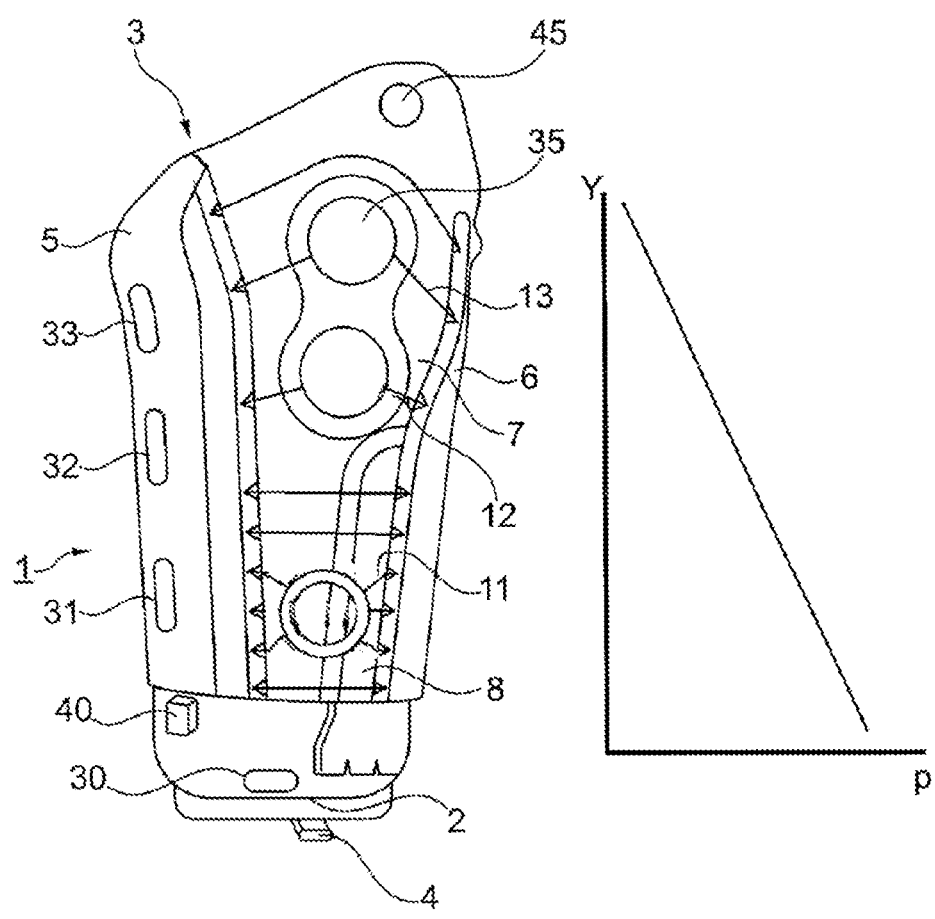
FIG. 1 shows a top view onto a prosthesis socket and a pressure distribution characteristic line.

In FIG. 1, in a top view, a prosthesis socket 1 is represented, which, in the represented embodiment example, is designed as a thigh socket for receiving a thigh stump. In principle, it is also possible to design the prosthesis socket 1 as a lower leg socket or as a prosthesis socket for an upper extremity. On its distal end, the prosthesis socket 1 has an end piece 2 which forms the distal closure of a receiving space for a limb stump. The distal end piece 2 lies opposite a proximal opening 3. The prosthesis socket 1 is formed substantially in the shape of a funnel; it surrounds substantially the entire circumference of the limb stump, which is not represented, and it forms a lower closure, so that a limb stump, optionally together with a liner pulled over the limb stump, is only insertable up to the distal end piece 2.

On the distal end piece, a connection means 4 for additional prosthesis components is arranged or connected. The closure means 4 are, for example, pyramid adapters, positive-locking receivers, screw receivers, bolts or other devices by means of which additional prosthesis components can be connected to the prosthesis socket 1. In the embodiment example of the prosthesis socket 1 as a thigh socket, a prosthetic knee joint is secured by means of the connection means 4 on the distal end piece 2.

In the design of the prosthesis socket as a lower leg socket, a prosthetic foot or a lower leg tube is secured as an additional prosthesis component on the connection means 4; in the design as a lower arm socket, a prosthetic hand is secured.

The end piece 2 can be designed as a flat plate or as a cup-shaped receiver and closure of the prosthesis socket 1. In addition to a preferably dimensionally-stable design of the end piece 2 made of a metal, a plastic or the like, for example, the end piece 2 can also be designed to be flexible. Support elements 5, 6, 7, 8 adjoin the end piece 2 in proximal direction, said support elements being either designed to form a single part with the end piece 2 or produced separately and connected thereto. The support elements 5, 6, 7, 8 are arranged so that they form a receiving space between themselves, in which the limb stump, not represented, can be inserted through the insertion opening 3. The support elements 5, 6, 7, 8 completely surround the limb stump. Due to the design in segments of the support elements 5, 6, 7, 8 and due to either a mobile mounting on the end piece 2 or due to an inherent resilience resulting, for example, from the material selection or a weakening of the material in the area of the end piece 2, it is possible to move the support elements 5, 6, 7, 8 apart from one another or towards one another in order to widen the prosthesis socket or to reduce the insertion opening 3 and the receiving space. The inner circumference of the prosthesis socket 1 is changed by the movement of the support elements due to the activation or deactivation of an actuator.

According to the represented embodiment example, on the front side of the prosthesis socket 1, three tensioning devices 11, 12, 13 are arranged, by means of which at least the lateral support element 6 can be moved in the direction of the medial support element 5. The orientation of the support element 7 is substantially frontal; an additional support element 8 is secured with a hinge to the end piece 2 and used for improved frontal bracing. The lateral support element 6 can be connected to the additional support element 8.

In the represented embodiment example, the tensioning devices or tensioning elements 11, 12, 13 are designed as cords, cables or ropes; it is also possible that the represented tensioning devices 11, 12, 13 which are designed in the form of a rope are instead in the form of a belt or else in the form of a rod, a chain, a perforated band or another traction means. It is essential that the tensioning device is suitable for moving the support devices towards one another, that is to say for applying traction forces, wherein, due to the flexible and preferably non-resilient design of the tensioning devices 11, 12, 13, predominantly circular forces are active. Due to the movement of the support elements 5, 6, 7, 8 towards one another, the inner circumference of the prosthesis socket is reduced.

The tensioning devices 11, 12, 13 are guided in eyelets on the mutually facing margins of the support elements 5, 6 and arranged like shoe laces. In total, three mutually independent tensioning devices 11, 12, 13 are arranged on the prosthesis socket 1, which are arranged with mutual offset with respect to one another in the proximal-distal direction, whereby it is possible that different pressures are exerted on the limb stump at different heights.

The tensioning devices 11, 12, 13 can be tensioned by means of an actuator, in the embodiment example a motor; for this purpose, the tensioning devices are wound on a roller which is coupled to the motor, for example, by means of a gear, so that relative small motors with high rotation speeds can be used, which results in a saving of installation space and weight. If the motors, which are not represented, are activated, the respective tensioning device 11, 12, 13 is wound, the support devices 5, 6, 7, 8 are moved towards one another, and the prosthesis socket 1 closes around the limb stump.

Moreover, in the prosthesis socket 1, a control device 40 is arranged, by means of which the actuators or motors (or the actuator or the motor, if only one actuator or motor is used) can be actuated. The control device 40 is connected to the actuators. Moreover, the control device 40 is connected to a switch 45, by means of which the opening or closing of the prosthesis socket 1 can be switched on. In addition to a manual operation and activation of the prosthesis socket by the switch 45 on the proximal end of the frontal support element 7, in the distal area of the receiving space, a contact sensor 30 is arranged, in the embodiment example represented, in the distal end area of the receiving space. If the contact sensor 30 is touched, a signal is transmitted to the control device 40, so that an activation of the actuator/motor or of the actuators/motors occurs automatically, in order to close the tensioning devices 11, 12, 13. The contact sensor 30 can also be designed as a simple switch.

Along at least one support element 5, pressure sensors 31, 32, 33 are arranged, by means of which the contact pressure of the support elements 5, 6, 7, 8 can be monitored. If preset pressures are reached, the respective actuator is deactivated by means of the control device 40. Advantageously, a pressure distribution is set, as shown in the right diagram in FIG. 1, in which an elevated pressure, which decreases in proximal direction, is applied in the distal area.

Moreover, an inertial sensor 35 can be connected on the prosthesis socket 1. The inertial sensor 35 acquires the position of the prosthesis socket 1 in space. Thereby, various types of information can be acquired, relating, for example, to the activity level, so that, depending on the respective detected activity, an adjustment of the contact pressure can occur by changing the inner circumference by opening or closing the tensioning devices 11, 12, 13.

In addition to the represented inertial sensor 35 or inertial angle sensor, which detects the orientation with respect to a fixed reference value, for example, the gravitational force, position sensors, acceleration sensors or other sensors can be arranged on the prosthesis socket 1 and coupled to the control unit 40, in order to obtain thereby information on the current activities. Also, a time switch device is arranged in the control unit 40, by means of which a time-controlled tensioning or relaxation of the tensioning devices 11, 12, 13 can be initiated.

Figure 2:
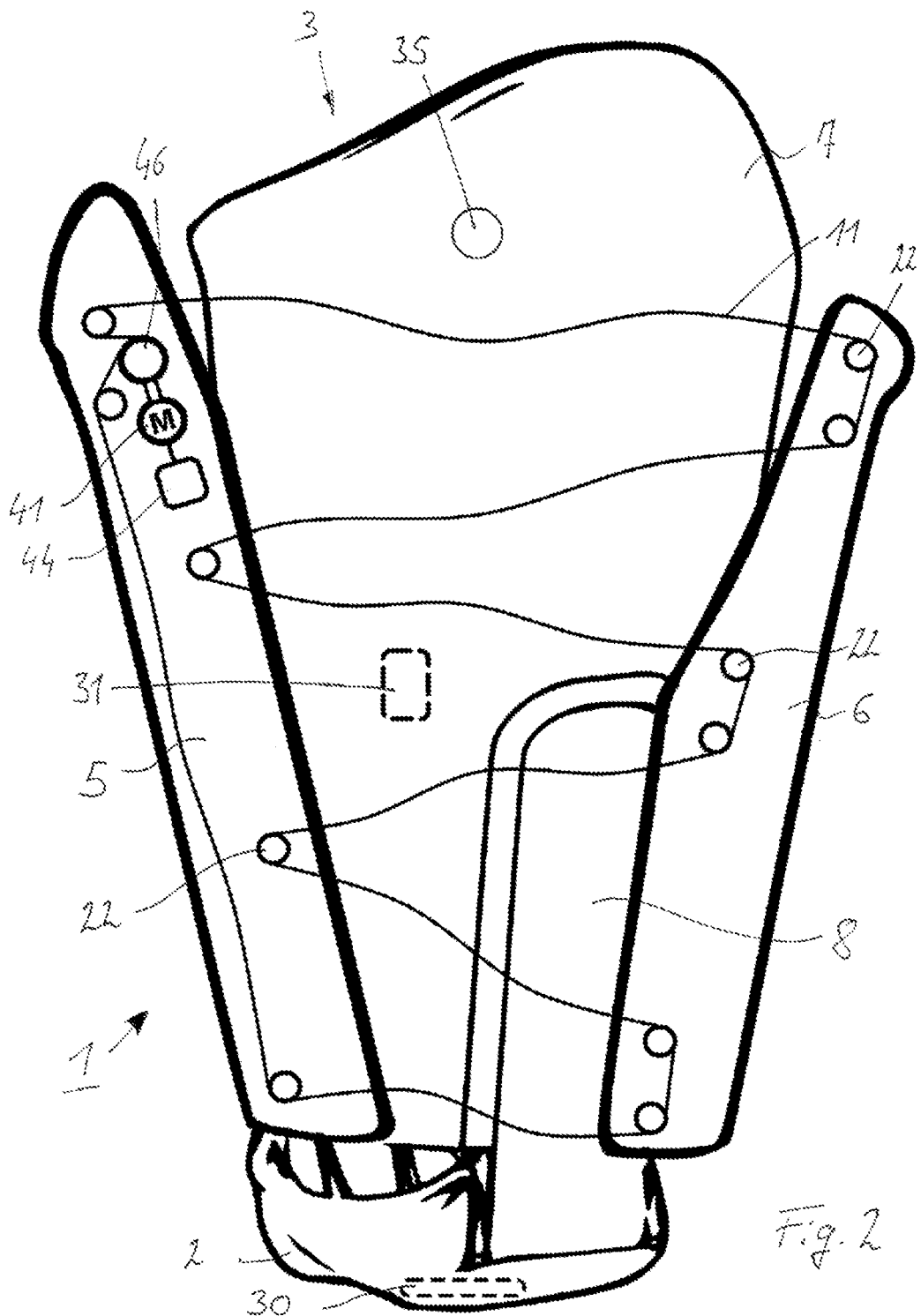
FIG. 2 shows an opened prosthesis socket with a tensioning device and a motor.

FIG. 2 shows a variant of the invention in a diagrammatic representation in the opened state. Identical reference numerals designate identical components. From FIG. 2, one can see that the two lateral support elements 5, 6 are flipped open medially-laterally, resulting in a widened insertion opening 3. Instead of multiple separate tensioning devices 11, 12, 13, only a single tensioning device 11 in the form of a cable or a cord is arranged on the outer circumference of the prosthesis socket 1. The uninterrupted tensioning device 11 is guided along deflection rollers 22 which are arranged at different levels or heights in the proximal-distal direction. The tensioning device 11 is guided so that it meanders like a hose around the deflection rollers 22, wherein the tensioning device 11 is rolled on a roller 46, when an actuator 41 is driven in the form of a motor in a corresponding rotation direction. A motor current sensor 44 which measures the applied motor current is associated with the motor 41. By means of the motor current, it is possible to detect the motor torque and thus the force with which the tensioning device 11 is tensioned. Based on the tension force of the tensioning device 11, it can be concluded that there is applied contact pressure of the support elements 5, 6, 7, 8 onto the limb stump.

In addition to the motor current sensor 44, a pressure sensor 31 is arranged on the inner side of the frontal support element 7, in order to be able to transmit an additional measurement value to the control unit 40 which is not represented.

Not represented is a rearward support element which is also arranged on the end piece 2 so that it overlaps the medial and lateral support elements 5, 6, resulting in a complete enclosure of the limb stump which is not represented.

On the bottom of the receiving space on the end piece 2, the distal contact sensor 30 is arranged. The support elements 5, 6, 7, 8 are pretensioned directed outwardly or designed to be resilient, so that, after relaxation of the tensioning device 11 by unwinding the tensioning device 11 from the roller 46, the prosthesis socket 1 opens.

Figure 3:
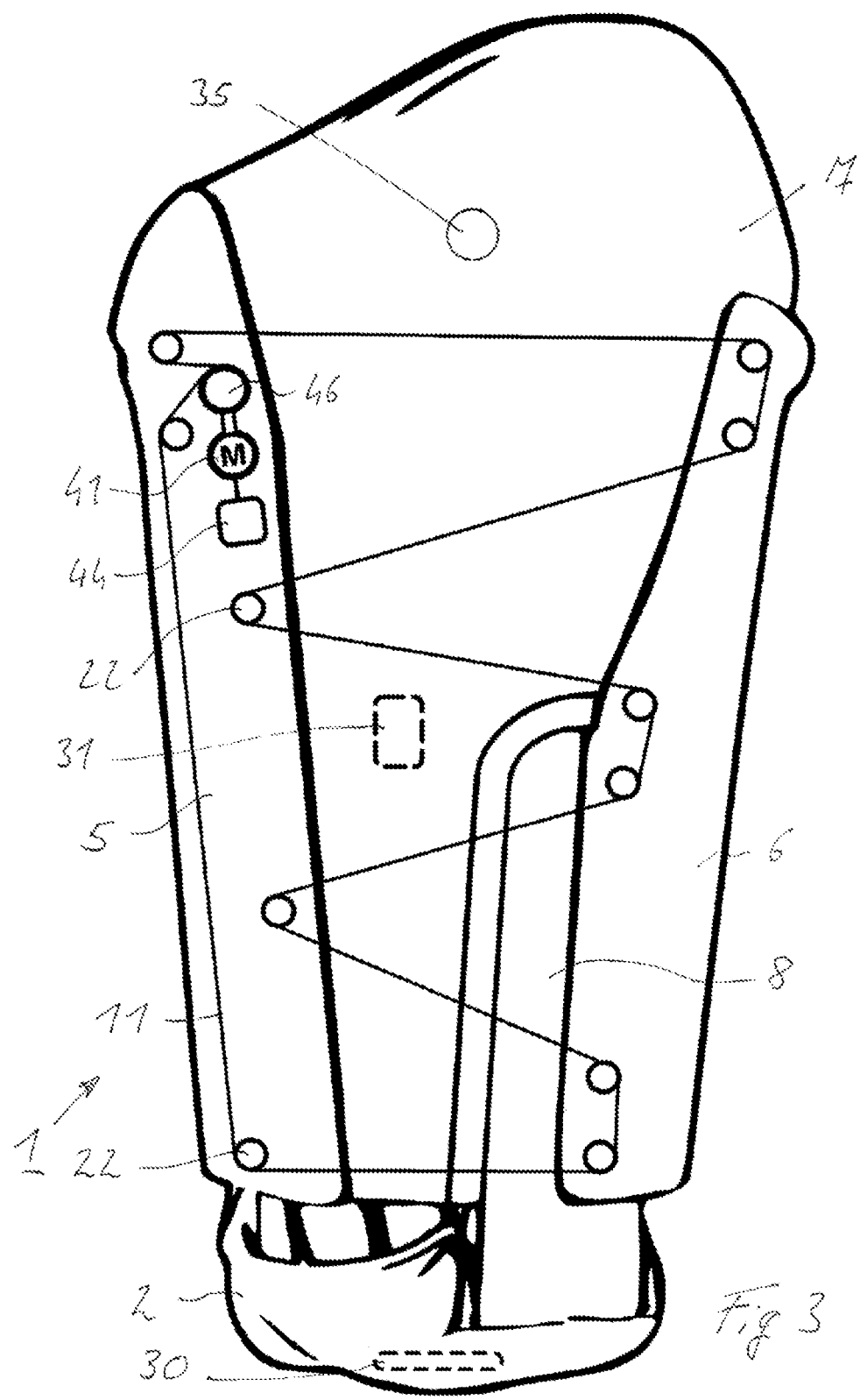
FIG. 3 shows a closed prosthesis socket according to FIG. 2.

FIG. 3 shows the prosthesis socket 1 according to FIG. 2 in a closed state. A limb stump which is not represented has been introduced through the insertion opening 3 in the receiving space and has activated the contact sensor 30. The motor 41 was put in operation due to the activation signal of the control unit 40 which is not represented. The tensioning device 11 was wound on the roller 46, until the motor current sensor 44 or the pressure sensor 31 transmits a signal to the control unit 40, until the desired or preset limit pressure is reached. The control unit 40 has switched off the motor 41 and holds the tensioning device 11 in the tensioned state. The tensioning device 11 is guided perpendicularly along the medial support element 4 in the proximal-distal direction, frontally crosses in the lower area of the support elements 5, 6, 7, 8 and is deflected by deflection rollers 22, resulting in a zig-zag arrangement or a zig-zag course between the medial support element 5 and the lateral support element 6. In the proximal end area, the tensioning device 11 crosses again frontally and is coupled to the roller 46 and wound there. In addition to a permanent application of a holding current to the motor 41, it is possible and provided that a mechanical locking device is associated with the tensioning device 11, so that the motor 41 can be switched off. For the unlocking, the mechanical locking device can then be unlocked and the motor 41 can be activated in a reverse direction of rotation in order to open the prosthesis socket 1.

Figure 4:
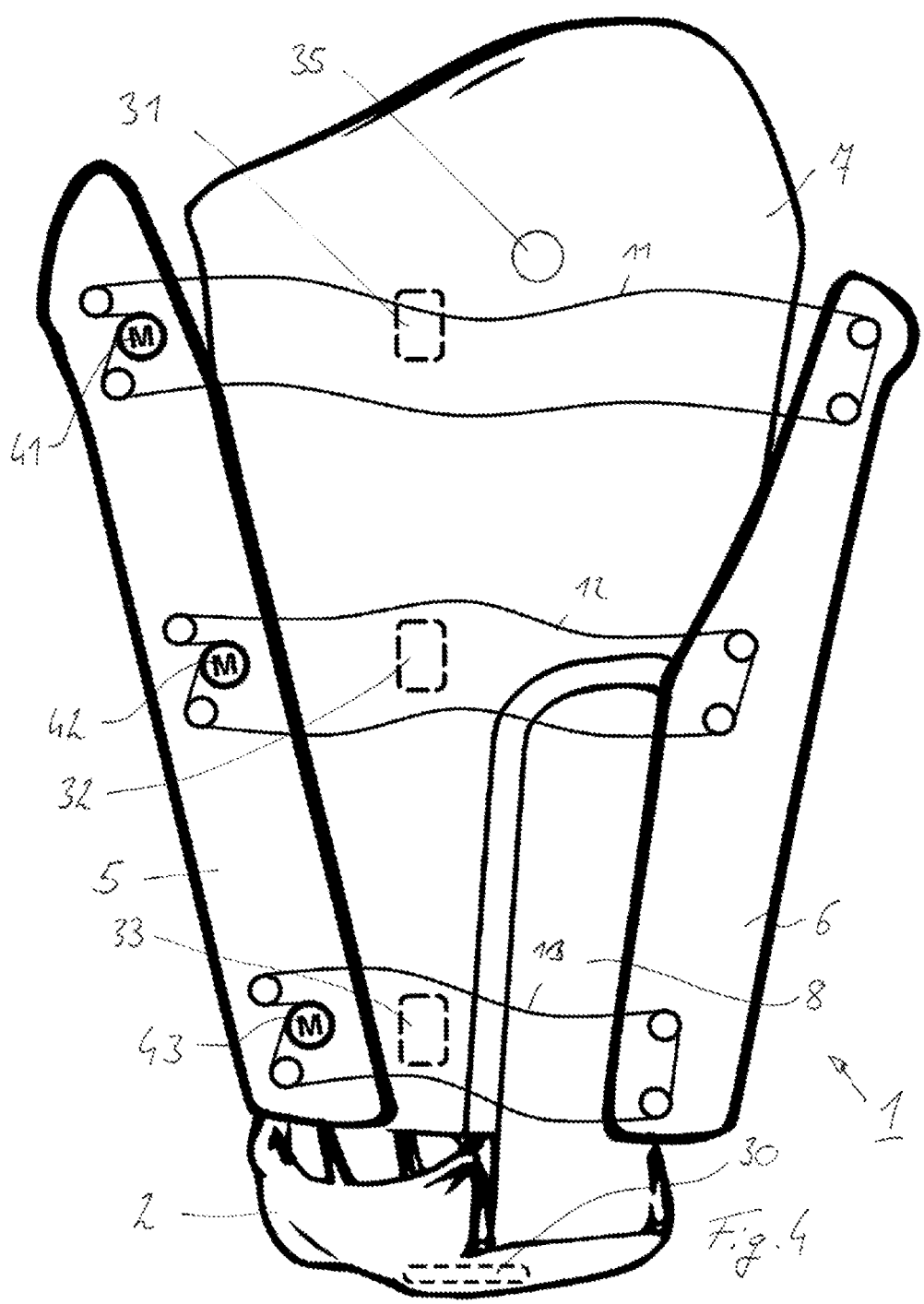
FIG. 4 shows an opened prosthesis socket with multiple tensioning devices and motors.

A variant of the embodiment according to FIG. 3 is shown in FIG. 4. Instead of only a single motor 41, three motors 41, 43 are secured at different heights in the proximal-distal direction on the prosthesis socket 1. A tensioning device 11, 12, 13 is associated with each motor 1. At the respective heights of the motors 41, 42, 43, pressure sensors 31, 32, 33 are arranged on the inner side of the prosthesis socket 1 in the receiving space, in the represented embodiment example on the frontal support element 7. The pressure sensors 31, 32, 33 can also be arranged on another support element 5, 6, 7, 8. In the same way, multiple sensors 31, 32, 33 can be arranged on each support element 5, 6, 7, 8; sensors can also be arranged at different heights on different support elements. It is also possible that, in addition to multiple sensors, multiple motor current sensors are associated with the respective motors 41, 42, 43.

All the motors 41, 42, 43 are connected to the control unit 40 which is not represented. If the sensor 30 or contact switch 30 is activated, the motors 41, 42, 43 are activated in such a manner that the tensioning devices 11, 12, 13 are wound, for example, on a motor shaft.

Figure 5:
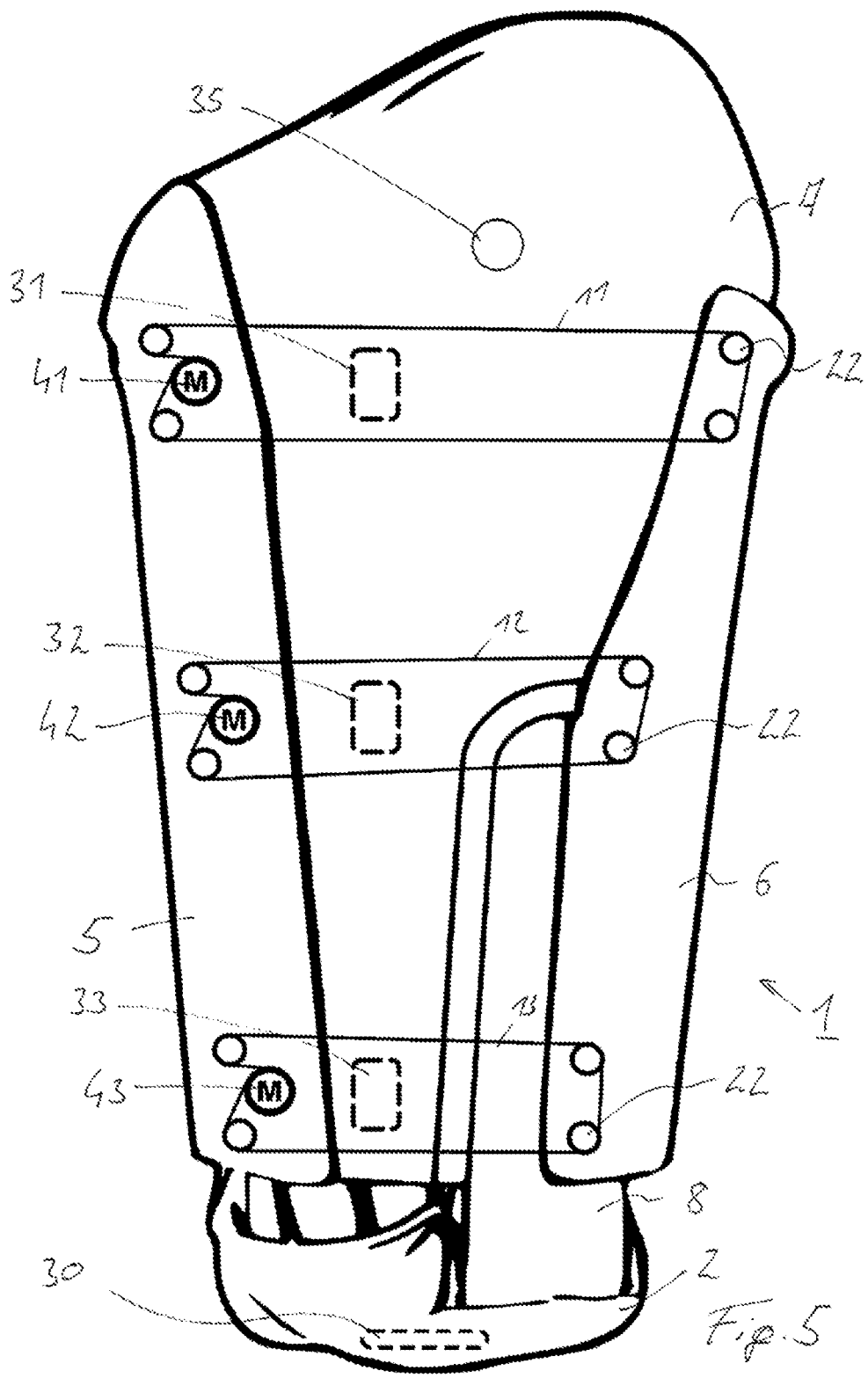
FIG. 5 shows a closed prosthesis socket according to FIG. 4.

In FIG. 5, the closed state is represented, after the motors 41, 42, 43 have tensioned the tensioning devices 11, 12, 13. The support elements 5, 6, 7, 8 have been moved towards one another until the respective sensor 31, 32, 33 has displayed the predetermined contact pressure. Then, the motors 41, 42, 43 are switched off accordingly, and the prosthesis socket 1 is closed.

Figure 6:
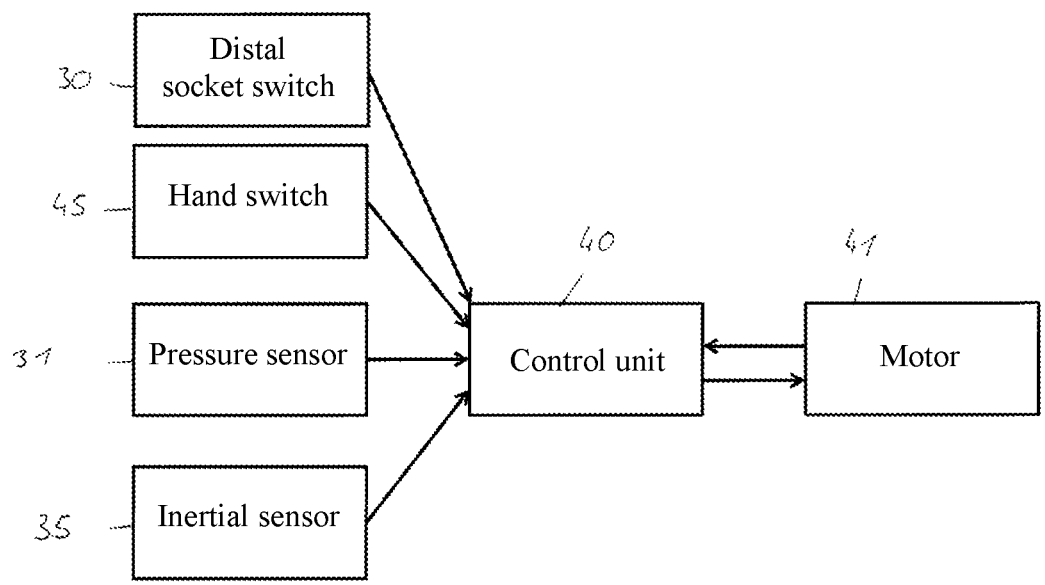
FIG. 6 shows a circuit diagram.

FIG. 6 shows a diagrammatic representation of the motor control. The control unit 40 is connected to the motor 41 or to the motors. Furthermore, the distal shaft connector 30, the manual switch 45, the pressure sensor(s) 31 and the inertial sensor 35 are connected to the control unit 40. Additional sensors or switches can also be connected to the control unit 40.

Based on the information from the sensors or commands via the switches, the control unit 40 activates the motor and tensions or relaxes the respective associated tensioning device.

The prosthesis socket according to the invention enables an automatic opening and closing by a corresponding activation or deactivation of an actuator or of multiple actuators which are connected to one or more tensioning devices, for example, to a lacing system or to multiple lacing systems. Instead of the activation of traction means which are rolled up and unrolled, the actuators can also activate and move other active elements such as levers, toothed wheels and toothed rods, sliders, spindles, spreading wedges, rings or clips, in order to bring about a change in inner circumference based on sensor data. In addition to a multi-part design of the prosthesis socket with several support elements which can be moved with respect to one another, the prosthesis socket can also be formed with only one single-part socket wall which has a slot or is wound up in the form of a coil like a torch. In a conical design, an opening or closing of the prosthesis socket can occur by shifting a ring or a clip along the longitudinal extent of the socket. Other measures for changing the inner circumference have already been described above. The prosthesis socket has the advantage, among others, that even in the case of variations of the limb stump volume or in the case of different limb stumps, a correct adjustment of the prosthesis socket to the limb stump can occur. Thus, it is no longer necessary to provide an individually molded prosthesis limb stump. In the basic state, the prosthesis socket is open, that is to say the support elements have been opened up. If the distal socket switch is activated, wherein the distal switch can be designed as a contact switch, a pressure switch, a mechanical switch or a proximity switch, the actuator is activated or the actuators are activated until the preset normal contact pressure of the socket wall or of the support elements on the limb stump has been reached. In this normal mode, the usual activities can be performed, for example walking or climbing stairs, in the case of a prosthesis of the lower extremity.

If high accelerations are detected over a certain time period, for example, by an acceleration sensor arranged on the prosthesis socket or on the prosthesis, one or more actuators are activated by means of the control unit, in order to reduce the inner circumference and optionally retension the tensioning device or the tensioning devices. The changing or tensioning process is continued until a preset contact pressure is reached, which appears suitable for the detected loading mode, for example, during sports activities.

As soon as elevated accelerations or forces are no longer detected and the absence of special loads has been detected over a certain time period, the contact pressure is reduced, in that the tensioning devices are released, volumes are reduced, the magnet is activated or deactivated, shape memory alloys are activated or deactivated, or other changes are carried out, until the normal pressure is reached again. The prosthesis socket opens due to resilience inherent in the support elements or the socket wall, or due to a separate reset device, for example, a spring, which loads the prosthesis socket with a force away from the limb stump.

If particularly small loads are detected again, or, on the other hand, if increases in contact pressure are detected, which are not caused by elevated acceleration values within the prosthesis or the prosthesis socket, for example, due to volume increases within the limb stump, the actuator or the actuators, starting from the normal mode, can relax the tensioning devices or other means in order to change the inner circumference, so that the prosthesis socket is in a relaxed mode with a lower contact pressure due to the increased inner circumference. This can occur, for example, during sitting or lying. Such states can be detected by means of acceleration sensors, position sensors and inertial sensors. If a movement start is detected, for example, by means of acceleration sensors, the motor tensions or the motors tension the tensioning device or the tensioning devices again, or the pump changes the volume in the inflatable pad, until the normal pressure is reached. The contact pressures can be determined again directly by means of pressure sensors or indirectly by means of motor current sensors or other sensors.

For the opening of the prosthesis socket, a manual switch is optionally activated, which relaxes the tensioning device or the tensioning devices to a maximum or activates the actuator to a maximum increase in inner circumference. If the actuators/motors or the actuator/motor fail(s), a mechanical unlocking device can be provided, by means of which the tensioning device can be completely relaxed or the inner circumference can be increased, to make it possible to take off the prosthesis socket.

Advantageously, the prosthesis socket is closed, as soon as it is displayed by means of the distal socket sensor or socket switch that the limb stump or the limb has been completely inserted. Alternatively or in addition to an automatic activation of the closure device, the socket can be closed by means of a separate close button, a magnetic switch, a smartphone, a tablet, a remote control or the like; for this purpose, the control unit is connected to a receiver module or to a corresponding contact with the switch. Voice control can also be provided, for opening or closing the prosthesis socket.

By alternating tensioning and relaxation of the tensioning devices, a massage effect can be provided for the received limb stump, which can be pleasant for the prosthesis user.

In addition to an adjustment based on activities, a tensioning or relaxation of the tensioning device in the context of a time program can occur, in order to avoid undesired pressure sites and injuries of the limb stump tissue. The sensors for the acquisition of the respective activities can be arranged both on the prosthesis socket and on the connected prosthetic device; the sensors located there, for example, inertial angle sensors, acceleration sensors, gyroscopes or angle sensors, can be used to bring about an adjusted change of the inner circumference, for example, by a tensioning or relaxation of tensioning devices.

Figure 7:
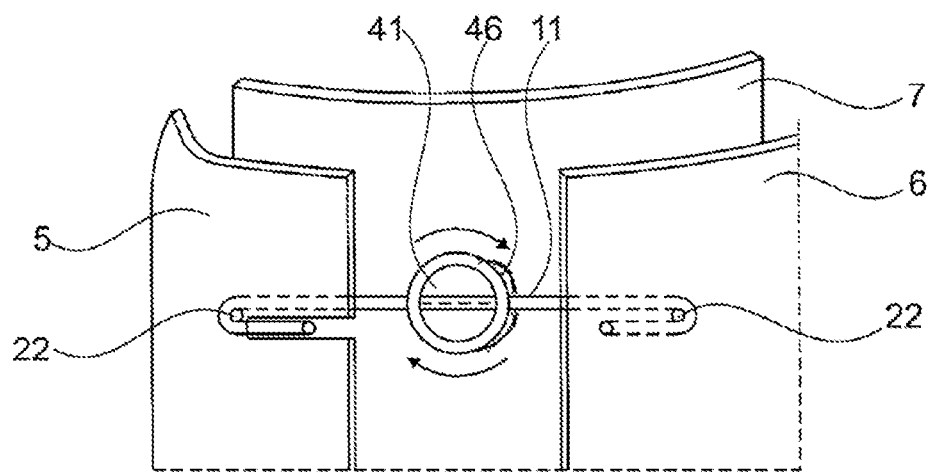
FIG. 7 shows a diagrammatic representation of a device for the opening of a socket.

FIG. 7 shows, in a detail view, a diagrammatic representation of a prosthesis socket 1 with three support elements 5, 6, 7, two of which are in each case arranged with mutual overlap. The support elements 5, 6 are arranged so that they form an inner circumference of the prosthesis socket, which is smaller than the outer circumference of a limb stump to be received or of a limb stump with prosthesis liner to be received. This can be brought about by a corresponding preformation or else by a pretensioning force which brings about a movement of the support elements 5, 6 in the direction of the limb stump. This can be, for example, a spring force which moves or pretensions the support elements 5, 6 hinged on an end piece in the direction of the limb stump which is not represented. On the third support element 7, an actuator 41 in the form of a motor is arranged, which is coupled to a roller 46 to which a tensioning element 11 in the form of a cable is connected. On the support element 7 to which the actuator 41 is connected, a pair of deflection elements 22 is also arranged, which are positioned on mutually facing sides of the roller 46. The cable 11 is connected to the roller 46 and guided around the deflection elements or deflection rollers 22, wherein the free ends of the cable 11, which are not connected to the roller 46, are again guided back in the direction of the roller 46. The guide of the cable 11 is thus U-shaped. In each case a free end is connected to the support element 5, 6 which overlaps the respective deflection roller 22. To the extent that the prosthesis socket consists of only two support elements, that is to say a gap or a slot is formed between a socket wall, which gap or slot is covered by the second support element 7, the free ends are in each case connected in the area of the mutually facing edges on the two sides of the roller 46.

Figure 8:
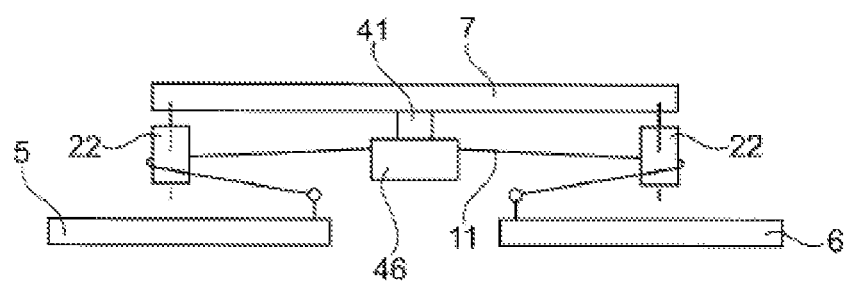
FIG. 8 shows a prosthesis socket in a detail view in closed position.
Figure 9:
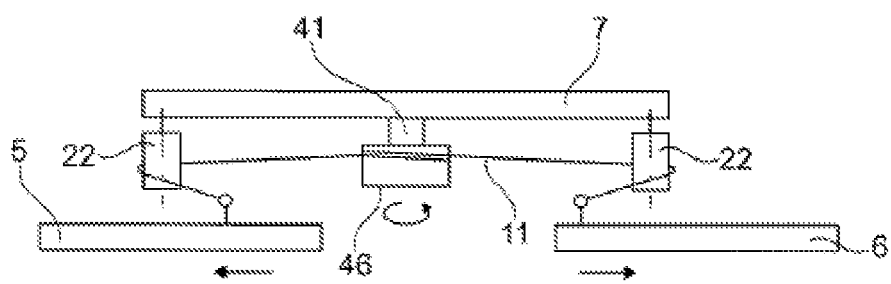
FIG. 9 shows the operating principle according to FIG. 8 in opened position.

FIG. 8 shows the construction of the spreading device according to FIG. 7 in the unopened state. The cable 11 is guided in opposite directions around the two deflection rollers 22, which are arranged spaced apart from one another, and back again to the edges of the two movable support elements 5, 6. There, the free ends of the cable 11 are connected to a respective connection site. The cable 11 is unrolled to a maximum; this means that the support elements 5, 6 are moved towards one another to a maximum, which results in a minimum inner circumference of the prosthesis socket. If the inner circumference is then to be increased, the actuator 41 in the form of a motor is activated, which is represented in FIG. 9. Due to the activation of the actuator 41, the roller 46 is set in rotation, the cable 11 is rolled up, and the connection sites with the free ends of the cable 11 are pulled in the direction of the respective deflection roller 22. Thereby, the gap or distance between the two support elements 5, 6 or the gap in a prosthesis socket wall is increased, whereby the inner circumference is increased, and the putting-on of the prosthesis socket is facilitated or the taking-off is facilitated or made possible. For the closing of the prosthesis socket 1, a reverse movement is brought about by the actuator 41, the cable 11 is unrolled, and the two support elements 5, 6 move again towards one another opposite the direction of the arrow according to FIG. 9. Thereby, the inner circumference is decreased, the pressure on the limb stump arranged within the prosthesis socket is increased, and an improved fit is achieved.

In principle, it is possible and provided that the above-described embodiment examples also function and are operated without sensors and without a control device, wherein the actuator 41 can then be activated either by a motor or manually; in particular, the manual opening or the opening by motor without sensors and control devices by activation of a motor or by manual activation of an actuator, for example of a toothed rod, of a slider, a threading, a roller, an adjustment of a spreading element, for example, of a ring, a clip or the like, makes it possible to increase the inner circumference. The reset occurs advantageously by a resilient reset force which is exerted on the opened prosthesis socket. A design without a sensor represents an independent solution and invention.

The invention claimed is:

1. A prosthesis socket comprising:
a plurality of support elements movable apart from one another for opening the prosthesis socket, the plurality of support elements defining a proximal insertion opening and an inner circumference configured to at least partially surround a limb stump, wherein the plurality of support elements exerts a resilient reset force on the limb stump;
at least one connection device configured to connect a prosthesis component to the prosthesis socket;
a plurality of tensioning devices arranged in a proximal-distal direction and operable independent of each other, wherein the plurality of tensioning devices are spaced from each other in the proximal-distal direction, and wherein the plurality of tensioning devices acts against the resilient reset force of the plurality of support elements to move apart the plurality of support elements;
at least one actuator operable to actuate the plurality of tensioning devices to move apart the plurality of support elements and change the inner circumference of the prosthesis socket;
a control device connected to the at least one actuator;
at least one sensor coupled to the control device and operable to generate control signals, wherein the at least one sensor comprises an inertial sensor; and
wherein the control device activates or deactivates the at least one actuator depending on received sensor signals.

2. The prosthesis socket according to claim 1, wherein the at least one actuator is designed as a drive for a pump, a sliding element, a lever, a winding device for traction members, a spreading element, a gear, a device for the activation of a shape memory alloy or of an electroactive polymer, or a switchable magnet.

3. The prosthesis socket according to claim 1, further comprising a switch, a contact switch or a sensor for the detection of an introduced limb stump, the switch, contact switch or sensor being arranged in a distal end area of the prosthesis socket.

4. The prosthesis socket according to claim 1, further comprising at least one of an internal pressure sensor and a motor current sensor configured for the acquisition of a pressure applied by a support element to the limb stump is arranged on a support element.

5. The prosthesis socket according to claim 1, wherein the control device is configured to be controlled directly with a switch, by gesture control or by remote control.

6. The prosthesis socket according to claim 1, wherein the at least one sensor further comprises at least one of a position sensor, an angle sensor, an acceleration sensor, a pressure sensor, and a switch.

7. The prosthesis socket according to claim 1, wherein the plurality of tensioning devices comprises at least three tensioning devices spaced from each other in the proximal-distal direction.

8. A prosthesis socket comprising:
a plurality of support elements movable apart from one another for opening the prosthesis socket, the plurality of support elements defining a proximal insertion opening and an inner circumference which is configured to at least partially surround a limb stump, wherein the plurality of support elements exerts a resilient reset force on the limb stump;
at least one connection device for a prosthesis component, which is connectable to the prosthesis socket;
at least one motor operable to modify the inner circumference of the prosthesis socket by moving apart the plurality of support elements and changing the inner circumference of the prosthesis socket;
at least one inertial sensor operable to detect a position of the prosthesis socket in space;
at least one motor current sensor or pressure sensor operable to generate motor sensor signals related to applied pressure of the prosthetic socket on the limb stump; and
a plurality of tensioning devices arranged in a proximal-distal direction and operable independently of each other, wherein the plurality of tensioning devices are spaced from each other in the proximal-distal direction, and wherein the plurality of tensioning devices acts against the resilient reset force of the plurality of support elements to move apart the plurality of support elements.

9. The prosthesis socket according to claim 8, wherein the prosthesis socket is designed in multiple parts with at least two support elements which are configured to receive the limb stump in between the at least two support elements.

10. The prosthesis socket according to claim 9, wherein the at least two support elements are formed or mounted resiliently.

11. The prosthesis socket according to claim 9, wherein the at least two support elements are designed to overlap one another in a circumferential direction.

12. The prosthesis socket according to claim 8, wherein a volume which is changeable by the at least one motor is arranged or formed on the prosthesis socket.

13. The prosthesis socket according to claim 8, wherein the plurality of tensioning devices are configured to change the inner circumference.

14. The prosthesis socket according to claim 13, wherein the plurality of tensioning devices are designed as a traction member, a pneumatically or hydraulically driven spreading or tensioning member, a longitudinally slidable spreading or closing element, a movable ring, a tilting element, or a rotatable actuation element.

15. The prosthesis socket according to claim 13, wherein the plurality of tensioning devices are guided in at least one of eyelets, channels or at least one deflection roller.

16. The prosthesis socket according to claim 13, wherein the plurality of tensioning devices act in a circumferential direction of the limb stump.

17. The prosthesis socket according to claim 8, wherein, in a closed state, a contact pressure applied to the limb stump by the actuator decreases in a proximal direction.

18. A method for controlling an adjustment of an inner circumference of a prosthesis socket according to claim 1, wherein, when at least one of a predetermined position of the limb stump and a compressive force exerted on the limb stump is detected by the at least one sensor, the actuator is activated or deactivated automatically.

19. The method according to claim 18 wherein the plurality of support elements are moved towards one another by their resilient behavior from a widened position to a tensioned position with an inner circumference which is reduced in comparison to the starting position.

20. A method for adjusting an inner circumference of a prosthesis socket, comprising:
opening the prosthesis socket by moving apart a plurality of support elements from one another with an actuator, wherein the plurality of support elements exerts a resilient pretensioning force on the limb stump and the actuator acts against the resilient pretensioning force to move apart the plurality of support elements;

changing an inner circumference of the prosthesis socket by relaxing a plurality of tensioning devices that operates independently against the resilient pretensioning force of the support elements or, the plurality of tension devices being arranged in a proximal-distal direction and spaced from each other in the proximal-distal direction;

changing the inner circumference of the prosthesis socket by tightening the plurality of tensioning devices that operate independently against the resilient pretensioning force of the support elements, wherein the spacing between the plurality of tensioning devices enables adjustment of the prosthesis socket along the proximal-distal direction; and detecting a position of the prosthesis socket using an inertial sensor.

* * * * *